(12) United States Patent
Liu et al.

(10) Patent No.: US 10,046,980 B2
(45) Date of Patent: Aug. 14, 2018

(54) BISMUTH-TITANIUM OXIDE NANOWIRE MATERIAL USED FOR PHOTOCATALYSIS, AND PREPARATION METHOD

(71) Applicant: CHONGQING UNIVERSITY OF ARTS AND SCIENCES, Chongqing (CN)

(72) Inventors: Bitao Liu, Chongqing (CN); Lu Li, Chongqing (CN)

(73) Assignee: CHONGQING UNIVERSITY OF ARTS AND SCIENCES, Chongqing (CN)

(*) Notice: Subject to any disclaimer, the term of this patent is extended or adjusted under 35 U.S.C. 154(b) by 0 days.

(21) Appl. No.: 15/559,061

(22) PCT Filed: Mar. 17, 2016

(86) PCT No.: PCT/CN2016/076586
§ 371 (c)(1),
(2) Date: Sep. 18, 2017

(87) PCT Pub. No.: WO2016/146070
PCT Pub. Date: Sep. 22, 2016

(65) Prior Publication Data
US 2018/0072586 A1    Mar. 15, 2018

(30) Foreign Application Priority Data
Mar. 18, 2015 (CN) .......................... 2015 1 0121107

(51) Int. Cl.
*C01G 29/00* (2006.01)
*C01G 23/04* (2006.01)
(Continued)

(52) U.S. Cl.
CPC .............. *C01G 29/00* (2013.01); *B22F 3/001* (2013.01); *B22F 3/10* (2013.01); *B82Y 40/00* (2013.01);
(Continued)

(58) Field of Classification Search
CPC . C01G 29/00; C01G 23/04; B22F 3/10; B22F 3/001; B82Y 40/00; C08F 26/10; C07C 233/03; C01P 2004/16
See application file for complete search history.

(56) References Cited

U.S. PATENT DOCUMENTS

2008/0105535 A1    5/2008 Nakato et al.

FOREIGN PATENT DOCUMENTS

| CN | 101623630 | 1/2010 |
| CN | 102826630 | 12/2012 |
| CN | 104645965 | 5/2015 |

OTHER PUBLICATIONS

Chen, Yuan, et al. "Facile synthesis of Bi nanoparticle modified TiO2 with enhanced visible light photocatalytic activity." Journal of Alloys and Compounds 651 (2015): 114-120.*

(Continued)

*Primary Examiner* — Richard M Rump
(74) *Attorney, Agent, or Firm* — JCIPRNET

(57) ABSTRACT

The present invention relates to bismuth-titanium oxide composite nanowires used for photocatalysis and a preparation method, belonging to the field of inorganic nanomaterials. The preparation of the bismuth-titanium oxide composite nanowires is: polyvinylpyrrolidone (PVP) and bismuth nitrate are added to N—N dimethylformamide (DMF), tetrabutyl titanate and acetylacetone are added after magnetic stirring has been performed for a period of time, continual stirring is performed for more than six hours, and a transparent, stable solution is obtained. Electrospinning is performed on the solution in an electrospinning generation device under certain conditions, and the obtained electrospinning precursor nano fibers are air-fired in a muffle furnace to remove organic matter. After being cooled to room temperature, the electrospinning precursor nano fibers are placed in a tube furnace to be reduced and sintered in a hydrogen atmosphere. The method is energy-saving and environmentally friendly, the conditions are easy to control, costs are low, and large-scale industrial production is easy. The obtained bismuth-titanium oxide nanowires exhibit good degradation activity on methyl orange under illumination, where the methyl orange degradation rate is reaching more than 95% in a reaction lasting for 20 minutes. The obtained bismuth-titanium oxide nanowires have wide application prospects in relation to sewage treatment.

4 Claims, 3 Drawing Sheets

(51) Int. Cl.
 *B82Y 40/00* (2011.01)
 *B22F 3/00* (2006.01)
 *B22F 3/10* (2006.01)
 *C07C 233/03* (2006.01)
 *C08F 26/10* (2006.01)

(52) U.S. Cl.
 CPC .......... *C01G 23/04* (2013.01); *C01P 2004/16* (2013.01); *C07C 233/03* (2013.01); *C08F 26/10* (2013.01)

(56) References Cited

OTHER PUBLICATIONS

"International Search Report (Form PCT/ISA/210)", dated Jul. 1, 2016, with English translation thereof, pp. 1-4.

\* cited by examiner

US 10,046,980 B2

BISMUTH-TITANIUM OXIDE NANOWIRE MATERIAL USED FOR PHOTOCATALYSIS, AND PREPARATION METHOD

CROSS-REFERENCE TO RELATED APPLICATION

This application is a 371 application of International PCT application serial no. PCT/CN2016/076586, filed on Mar. 17, 2016, which claims the priority benefit of Chinese application no. 201510121107.6, filed on Mar. 18, 2015. The entirety of each of the abovementioned patent applications is hereby incorporated by reference herein and made a part of this specification.

BACKGROUND OF THE INVENTION

Technical Field

The present invention generally relates to the technical field of inorganic nanomaterials and environmental pollution control, and particularly to a bismuth-titanium oxide nanowire material having a high photocatalytic activity and used in the degradation of pollutants (dyes) and a preparation method thereof.

Background Technology

With the rapid expansion of population and the rapid development of industry, the environmental pollution has become a primary problem affecting the production and life of human being, and an environmental pollution control is regarded as the affair of top priority by the government of each country at present and in the next few years. Particularly, in the printing and dying industry, a large discharging amount of water-soluble azo dyes such as methyl orange causes the water quality, which is critical to human survival, to deteriorate daily. The pollutants are difficult to be biodegraded. Once entering the water body, the hazard is long persisting because the natural degradation in the water body is slow. By means of a photocatalytic reaction, the pollutants can be mineralized into various inorganic ions under illumination. Therefore, the photocatalytic reaction receives great attention in the environmental pollution control, and the development of photocatalysts has become a research hotspot in China and other countries.

Due to the small size, large specific surface area, incomplete surface atom coordination and other characteristics, nano-titanium oxide has many surface active sites, thereby forming uneven atomic steps. When used as a catalyst, the contact area with the reactants is increased. Therefore, compared with a conventional catalyst, nano-titanium oxide has a higher catalytic activity. In the field of photocatalysis, the nano-titanium oxide catalyst can lead to the final decomposition of harmful organic substances in the water, so as to avoid the environmental pollution caused therefrom. Studies show that the reaction rate with nanometer titanium oxide is 100-1000 times of that of bulk titanium oxide material. Nanometer titanium oxide causes almost no light scattering compared with ordinary particles, so it is one of the most promising photocatalysts.

Up to now, the performance of titanium oxide has been improved by preparing a wide variety of titanium oxide composite materials, such as tin oxide-titanium oxide composite materials and zinc oxide-titanium oxide composite materials, etc. Although there are many ways, but there are still some shortcomings. The degradation efficiency of the currently obtained titanium oxide composite material on the pollutants is still needed to be improved. It is critical to the development of the photocatalysis technology to find a cheap, environmentally-friendly photocatalytic material having high catalytic activity.

SUMMARY OF THE INVENTION

Accordingly, in order to overcome the defects existing in the conventional art at present, the present invention relates to a bismuth-titanium oxide nanowire material having high degradation activity for the dye methyl orange.

The present invention further relates to a method for preparing the bismuth-titanium oxide nanowire material.

The present invention is accomplished through the following technical solutions.

A bismuth-titanium oxide composite nanowire material used for photocatalysis is provided, which the material has a microstructure that is a 200 nm-diameter porous linear structure, and includes metal bismuth of JCPDS No. 44-1246 and titanium oxide of JCPDS No. 21-1272 having a rutile structure. Studies show that during the photodegradation reaction, a photo-induced charge trapping center is formed, which inhibits the recombination of electron-hole pairs, such that the bismuth-titanium oxide composite nanowires have significant catalytic degradation effect on the dye methyl orange.

A method for preparing the bismuth-titanium oxide nanowires is provided, which the preparation is carried out through an electrospinning process. The method is energy-saving and environmentally friendly, the conditions are easy to control, the raw materials are widely available, costs are low, and the large-scale industrial production is easy. The obtained bismuth-titanium oxide nanowires have wide application prospects in relation to an pollutant treatment. The method includes specifically the steps of (1) adding polyvinylpyrrolidone (PVP) and bismuth nitrate to N—N dimethylformamide (DMF), adding tetrabutyl titanate and acetylacetone after magnetic stirring has been performed for a period of time, continuing the magnetic stirring for more than six hours, and obtaining a transparent and stable sol solution;

(2) electrospinning the sol solution obtained in Step (1) in an electrospinning generation device under certain conditions, to obtain electrospinning precursor nanofibres;

(3) air-firing the electrospinning precursor nanofibres obtained in Step (2) in a muffle furnace at a ramping rate of 5° C./min to remove organic matter; and (4) after cooling to room temperature, reducing and sintering the electrospinning precursor nanofibres in a tube furnace in a hydrogen atmosphere.

In the present invention, the transparent and stable solution in Step (1) means a solution in which no insoluble matter is observed after the magnetic stirring has been continued for more than six hours. The conditions for the electrospinning process in Step (2) include an ambient temperature of 20° C. or greater, a humidity of 85% RH or less, a spinning voltage of 8-25 KV, a needle diameter of the electrospinning generation device of 0.6-1.2 mm, and a distance between the needle and a receptor of 15-25 cm. During the baking process in the muffle furnace in Step (3), the temperature is raised stepwisely; and specifically, the temperature is raised from room temperature to 200° C. at a ramping rate of 5° C./min and then to 600° C. for 2 hours at a ramping rate of 10° C./min and finally naturally cooled to room temperature. During the baking process in the tube furnace in Step (4), the baking process occurs in a hydrogen atmosphere, and the temperature is raised from room temperature to 200° C. at a ramping rate of 5° C./min and then to 600° C. for 2 hours at a ramping rate of 10° C./min and finally naturally cooled to room temperature.

Compared with the conventional art, the present invention has the following advantageous effects.

In the method of the present invention, electrospinning is employed in the preparation process. The raw materials are readily available, and a composite material is obtained by hydrogen reduction. The whole experiment process is simple, the operation is convenient, and the large-scale production of the product is realized. The obtained bismuth-titanium oxide nanowires are uniform and continuous, have a large aspect ratio, and have a good catalytic degradation effect on the dye methyl orange, as indicated by the fact that about 35-40% of methyl orange is degraded every 5 minutes, and the degradation rate reaches about 97% in a reaction lasting for 15 minutes.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
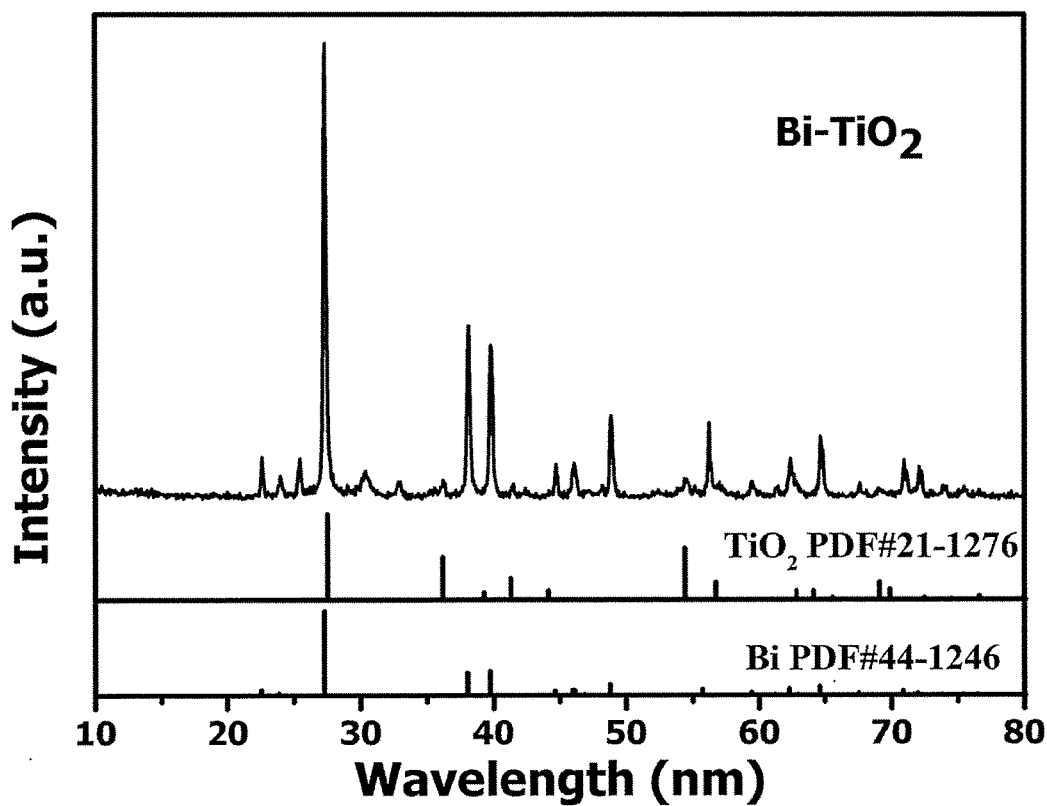
FIG. 1 is an XRD pattern of prepared bismuth-titanium oxide nanowires.
Figure 2:
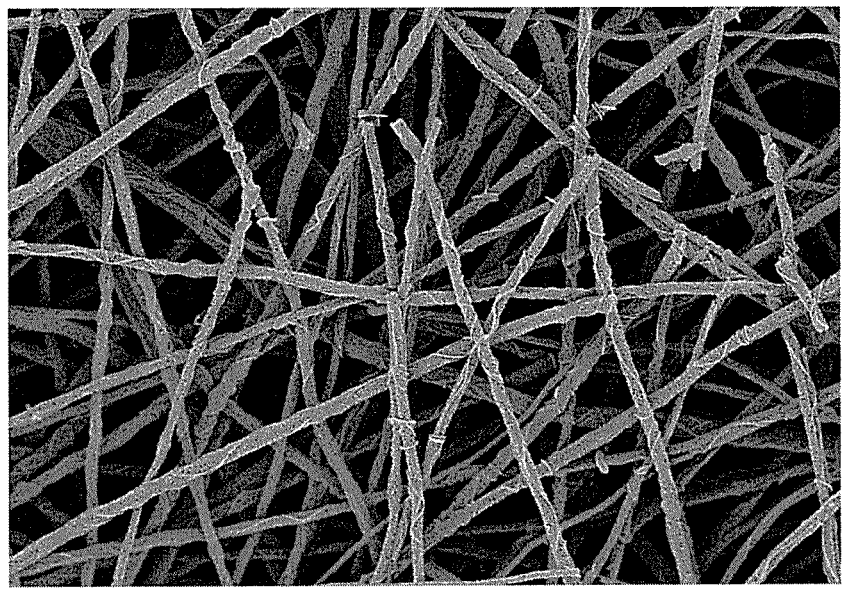
FIG. 2 is an SEM image of prepared bismuth-titanium oxide nanowires.
Figure 3:
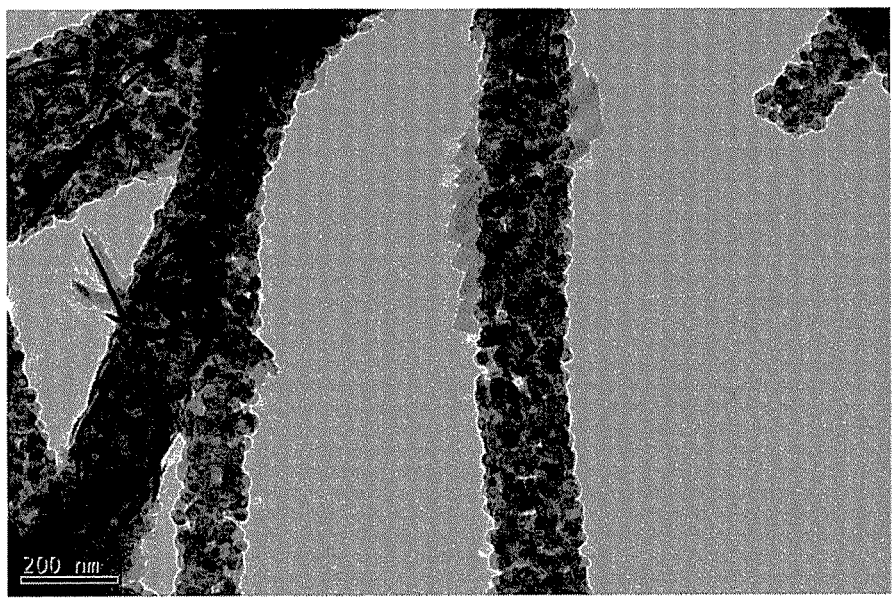
FIG. 3 is a TEM image of prepared bismuth-titanium oxide nanowires.
Figure 4A:
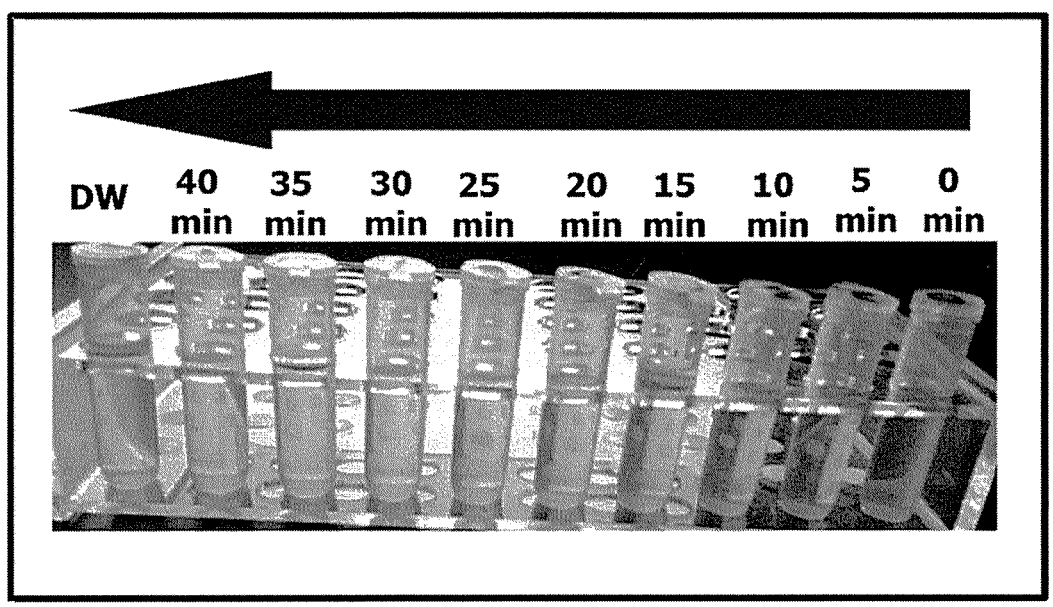
FIG. 4A and FIG. 4B show a photocatalytic effect of prepared bismuth-titanium oxide nanowires on degradation of methyl orange.
Figure 4B:
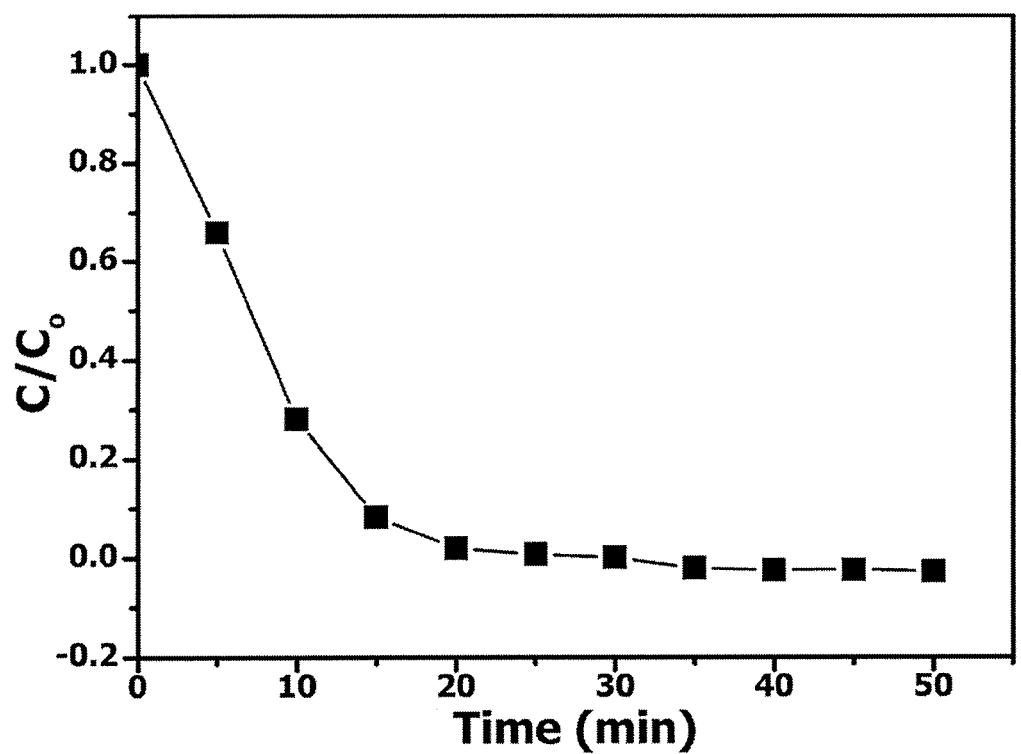

The present invention will be further described with reference to examples. The production techniques of the present invention are readily practiced by those skilled in the art. The present examples are carried out under the premise of the technical solution of the present invention, and detailed implementations and processes are given; however, the scope of the present invention is not limited to the following examples. The experimental methods in the examples for which no specific conditions are given are generally performed in accordance with conventional conditions or in accordance with the conditions recommended by the manufacturer.

Example 1

0.6 g of polyvinylpyrrolidone (PVP) and 4 g of bismuth nitrate were respectively weighed by an electronic balance and added to a beaker where 8 g N—N dimethylformamide (DMF) had already added, and magnetically stirred for 30 minutes. Then, 4 g of tetrabutyl titanate and 0.4 g of acetylacetone were added and stirred continuously for 6 hours so as to obtain a transparent and stable sol solution.

The sol solution was transferred to and electrospun in an electrospinning generation device. During the electrospinning process, the ambient temperature was controlled to be at 35° C., the humidity was controlled to be about 80% RH, the voltage was controlled to be 15 KV, the needle diameter was controlled to be 0.9 mm, and the reception distance was controlled to be about 15 cm. After the electrospinning process was completed, electrospinning precursor nanofibres were obtained.

The obtained nanofibres were collected to a crucible by forceps/tweezers and transferred to a muffle furnace. The obtained nano fibres were heated from room temperature to 200° C. at a ramping rate of 5° C./min and then to 600° C. for 2 hours at a ramping rate of 10° C./min and finally naturally cooled to room temperature.

The sintered nanowires were transferred to a tube furnace, and hydrogen was introduced. The sintered nanowires were heated from room temperature to 200° C. at a ramping rate of 5° C./min and then to 600° C. for 2 hours at a ramping rate of 10° C./min and finally naturally cooled to room temperature.

Photocatalytic Performance Test of the Material 0.2 g of bismuth-titanium oxide nanomaterial was accurately weighed, added to 500 ml of a methyl orange (MO) solution (40 mg/L), and then ultrasonically dispersed. The resultant suspension was stirred in the dark for 1 hour to allow the material to reach adsorption equilibrium. After equilibrium was reached, 3 ml of the suspension was removed, and the remaining suspension was poured into a 500 ml quartz tube, and then placed into a photocatalytic reactor. Under illumination with a 500 W high-pressure mercury lamp, for every 5 min, 3 ml of the suspension was removed and transferred to a centrifuge tube, and the total reaction time was 55 min. After the reaction, the samples taken were separated by centrifugation, and the absorbency of the supernatant at about 465 nm was determined by a UV-visible spectrophotometer. Such absorbencies reflected the concentration of the remaining methyl orange after each degradation period, thereby reflecting the degradation effect of the bismuth-titanium oxide photocatalyst prepared through the present method on methyl orange.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for preparing a bismuth-titanium oxide nanowire material, wherein the bismuth-titanium oxide nanowire material comprises a microstructure of a 200 nm-diameter porous linear structure, and a composition of the bismuth-titanium oxide nanowire material comprises a metal bismuth of JCPDS No. 44-1246 and a titanium oxide having a rutile structure of JCPDS No. 21-1272, and the method comprises:
   (1) adding polyvinylpyrrolidone (PVP) and bismuth nitrate to N—N dimethylformamide (DMF), adding tetrabutyl titanate and acetylacetone after magnetic stirring, continuing the magnetic stirring for more than six hours, and obtaining a transparent and stable sol solution;
   (2) electrospinning the transparent and stable sol solution obtained in Step (1) in an electrospinning generation device to obtain electrospinning precursor nanofibres;
   (3) air-firing the electrospinning precursor nanofibres obtained in Step (2) in a muffle furnace at a ramping rate of 5° C./min to remove organic matter; and
   (4) after cooling to room temperature, reducing and sintering the electrospinning precursor nanofibres obtained in Step (3) in a tube furnace in a hydrogen atmosphere.

2. The method for preparing a bismuth-titanium oxide nanowire material according to claim 1, wherein conditions for a process of electrospinning in Step (2) comprise an ambient temperature of about 20° C. or greater, a humidity of about 85% RH or less, a spinning voltage of about 8 KV to about 25 KV, a needle diameter of about 0.6 mm to about 1.2 mm, and a distance between the needle and a receptor of about 15 cm to about 25 cm.

3. The method for preparing a bismuth-titanium oxide nanowire material according to claim 1, wherein during a process of air-firing in the muffle furnace in Step (3), a temperature thereof is raised stepwisely, wherein the temperature is raised from a room temperature to 200° C. at a ramping rate of 5° C./min and then raised to 600° C. for 2 hours at a ramping rate of 10° C./min, and finally naturally cooled to the room temperature.

4. The method for preparing a bismuth-titanium oxide nanowire material according to claim 1, wherein during a process of reducing and sintering in the tube furnace in Step (4), the process of reducing and sintering occurs in a hydrogen atmosphere, and a temperature thereof is raised from a room temperature to 200° C. at a ramping rate of 5° C./min and then raised to 600° C. for 2 hours at a ramping rate of 10° C./min, and finally naturally cooled to the room temperature.

* * * * *